US 6,558,375 B1

(12) United States Patent  
Sinofsky et al.

(10) Patent No.: US 6,558,375 B1
(45) Date of Patent: May 6, 2003

(54) CARDIAC ABLATION INSTRUMENT (75) Inventors: Edward L. Sinofsky, Dennis, MA (US); Norman E. Farr, Monument Beach, MA (US); Lincoln S. Baxter, Centerville, MA (US)

(73) Assignee: CardioFocus, Inc., Norton, MA (US)

( * ) Notice: Subject to any disclaimer, the term of this patent is extended or adjusted under 35 U.S.C. 154(b) by 56 days.

(21) Appl. No.: 09/616,777

(22) Filed: Jul. 14, 2000

(51) Int. Cl.⁷ .............................................. A61B 18/18
(52) U.S. Cl. ........................ 606/16; 606/13; 606/15
(58) Field of Search .......................... 606/2–3, 7, 9, 606/10–16, 17; 607/89, 88

(56) References Cited

U.S. PATENT DOCUMENTS

| | | | |
|---|---|---|---|
| 4,422,719 A | * 12/1983 | Orcutt ........................ 350/96.3 |
| 4,699,147 A | 10/1987 | Chilson et al. ............. 128/642 |
| 4,842,390 A | * 6/1989 | Sottini ........................ 385/43 |
| 5,071,417 A | 12/1991 | Sinofsky ..................... 606/8 |
| 5,151,096 A | 9/1992 | Khoury ....................... 606/15 |
| 5,151,097 A | * 9/1992 | Daikuzono .................. 606/15 |
| 5,163,935 A | 11/1992 | Black et al. ................. 606/17 |
| 5,207,669 A | * 5/1993 | Baker et al. ................. 606/7 |
| 5,219,346 A | 6/1993 | Wagnieres et al. ........... 606/16 |
| 5,368,564 A | 11/1994 | Savage ........................ 604/95 |
| 5,411,025 A | 5/1995 | Webster, Jr. ................ 128/642 |
| 5,431,168 A | 7/1995 | Webster, Jr. ................ 128/658 |
| 5,431,647 A | 7/1995 | Purcell, Jr. et al. ........... 606/16 |
| 5,441,497 A | 8/1995 | Narcisco, Jr. ............... 606/15 |
| 5,464,404 A | 11/1995 | Abela et al. ................. 606/15 |
| 5,471,982 A | 12/1995 | Edwards et al. ............. 128/642 |
| 5,500,012 A | 3/1996 | Brucker et al. ............. 607/122 |
| 5,507,725 A | 4/1996 | Savage et al. ................ 604/95 |
| 5,536,265 A | 7/1996 | van den Bergh et al. ....... 606/2 |
| 5,542,928 A | 8/1996 | Evans et al. ................. 604/113 |
| 5,628,313 A | 5/1997 | Webster, Jr. ................ 128/642 |
| 5,632,767 A | * 5/1997 | Sinofsky ..................... 607/89 |
| 5,643,253 A | 7/1997 | Baxter et al. ................. 606/17 |
| 5,649,923 A | 7/1997 | Gregory et al. | |
| 5,681,280 A | 10/1997 | Rusk et al. .................. 604/95 |
| 5,688,264 A | * 11/1997 | Ren et al. .................... 606/15 |
| 5,722,401 A | 3/1998 | Pietroski et al. ............ 128/642 |
| 5,728,092 A | * 3/1998 | Doiron et al. ............... 606/15 |
| 5,772,590 A | 6/1998 | Webster, Jr. ................ 600/374 |
| 5,779,646 A | 7/1998 | Koblish et al. ............. 600/567 |
| 5,782,239 A | 7/1998 | Webster, Jr. ................ 128/642 |
| 5,782,899 A | 7/1998 | Imran ......................... 607/122 |
| 5,800,482 A | 9/1998 | Pomeranz et al. .......... 607/101 |

(List continued on next page.)

FOREIGN PATENT DOCUMENTS

| | | |
|---|---|---|
| DE | 94 11 754.3 | 12/1994 |
| EP | 0 792 664 A2 | 9/1997 |
| EP | 0 792 664 A3 | 6/1998 |
| EP | 1 072 231 A1 | 1/2001 |
| WO | WO 94/26184 | 11/1994 |
| WO | WO 96/07451 | 3/1996 |
| WO | WO 01/13812 A1 | 3/2001 |

*Primary Examiner*—Roy D. Gibson
*Assistant Examiner*—Pete J Vrettakos
(74) *Attorney, Agent, or Firm*—Thomas J. Engellenner; Lisa J. Michaud; Nutter McClennen & Fish LLP (57) ABSTRACT

The present invention is directed to a hand held cardiac ablation instrument and methods for irradiating a target ablation site. The instrument can include at least one light transmitting optical fiber and a light diffusing element to create a circumferential or curvilinear lesion. A handle is provided for manual application. The handle can be substantially coaxial or otherwise aligned with the center of the circumferential housing. Light travelling through the light transmitting optical fiber or fibers is scattered in a circular pattern by the light diffusing element. The light diffusing element can include a scattering medium, a reflective end cap, and a reflective surface diametrically opposed to the target ablation site, that interact to provide a substantially uniform distribution of laser radiation throughout the circular target region.

32 Claims, 6 Drawing Sheets

U.S. PATENT DOCUMENTS

| | | |
|---|---|---|
| 5,807,395 A | 9/1998 | Mulier et al. .................. 606/41 |
| 5,823,955 A | 10/1998 | Kuck et al. .................. 600/374 |
| 5,830,209 A | 11/1998 | Savage et al. ................. 606/15 |
| 5,833,682 A | 11/1998 | Amplatz et al. .............. 606/15 |
| 5,836,941 A * | 11/1998 | Yoshihara et al. ............ 606/15 |
| 5,860,974 A | 1/1999 | Abele .......................... 606/41 |
| 6,315,775 B1 * | 11/2001 | Thielen et al. ................ 606/16 |

* cited by examiner

CARDIAC ABLATION INSTRUMENT

BACKGROUND OF THE INVENTION

The present invention relates to a cardiac ablation instrument for endo or epicardial ablation of tissue for the treatment of cardiac conditions, and, in particular, to a handheld cardiac ablation instrument which provides uniform radiation. Methods of ablating cardiac tissue are also disclosed.

Cardiac rhythm irregularity, i.e., fibrillation, is a pathological condition of the heart muscle that can be present in either the atria or the ventricles. Atrial fibrillation is an atrial arrhythmia characterized by rapid randomized contractions of the atrial myocardium, causing an irregular, often rapid ventricular rate. The regular pumping function of the atria is replaced by a disorganized, ineffective quivering caused by chaotic conduction of electrical signals through the upper chambers of the heart. Atrial fibrillation is often associated with other forms of cardiovascular disease, including congestive heart failure, rheumatic heart disease, coronary artery disease, left ventricular hypertrophy, cardiomyopathy or hypertension.

Ventricular Tachycardia (fibrillation) is an arrhythmia characterized by fibrillary contractions of the ventricular muscle due to rapid repetitive excitation of the myocardial fibers without coordinated contraction of the ventricles. The ventricles beat at an abnormally rapid rate, significantly interfering with the pumping of oxygenated blood throughout the body. When this occurs, the ventricles lack sufficient time to fill with blood prior to each contraction. As a result, less blood is pumped out of the heart and less oxygen is carried to the tissues and organs of the body.

Several different ablation techniques are known for treating cardiac arrhythmias. A common technique, known as the Maze technique, requires open chest surgery to segment the atrial tissue in a manner that prevents the heart from sustaining the atrial fibrillation. By providing linear ablations at selected locations in the atrial tissue, electrical conductivity from one segment to another can be blocked and the resulting segments become too small to sustain the fibrillatory process on their own.

Conventional instruments employ a radio frequency ablating device having multiple electrodes with gaps between each electrode. These instruments require careful delivery of energy to the surgical site in order to form long, thin lesions in the heart tissue. The lesions must be well defined within the heart to be effective. The gaps in between the electrodes create a break in the energy, thereby creating a potential for gaps in the lesion pattern, which are known to be proarrhythmic and can lead to atrial flutter. In addition, if the energy is not uniformly transmitted to the target site, hot spots can form causing severe tissue damage or blood coagulation (clots).

Accordingly, there exists a need for a cardiac ablation instrument that provides uniform radiation along a curved path with minimal risks of tissue damage, coagulum formation, and overheating.

SUMMARY OF THE INVENTION

The present invention is directed to a hand held cardiac ablation instrument for irradiating a target ablation site. The hand held instrument is especially useful in open chest or port access cardiac surgery for rapid and efficient creation of circumferential and curvilinear lesions. The invention is useful for performing both endocardial and epicardial ablations. The instrument is designed to create lesions in the atrial tissue in order to electrically decouple tissue segments on opposite sides of the lesion. The hand held instrument can include at least one light transmitting optical fiber and a light diffusing element which creates the circumferential or curvilinear lesion. The light diffusing element can be resiliently deformable. A handle is provided for manual application. The handle can be substantially coaxial or otherwise aligned with the center of the circumferential housing.

In one aspect of the invention, an instrument is disclosed that permits uniform irradiation along a curved surface on a hand held device. Light travelling through the light transmitting optical fiber or fibers is scattered in a circular pattern by the light diffusing element. The light diffusing element can include a scattering medium and a reflective end cap that interact to provide a substantially uniform distribution of laser radiation throughout the curvilinear target region. The light diffusing element can also include a reflective coating applied to one side of the light diffusing element such that the coating lies substantially diametrically opposed to the target ablation site.

BRIEF DESCRIPTION OF THE DRAWINGS

The invention will be more fully understood from the following detailed description taken in conjunction with the accompanying drawings, in which like reference numerals designate like parts throughout the figures, and wherein.

DETAILED DESCRIPTION

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

As will be described with reference to the detailed embodiments below, the present invention is a hand held cardiac ablation instrument which is adapted to treat patients with atrial arrhythmia by uniformly irradiating a target ablation site.

The terms "circumferential" and "curvilinear," including derivatives thereof, are herein intended to mean a path or line which forms an outer border or perimeter that surrounds and thereby defines a region of space. The path may contain an opening or gap. Still further, a circumferential path or element may include one or more of several shapes, and may be for example, circular, annular, oblong, ovular, elliptical, or toroidal.

Figure 1:
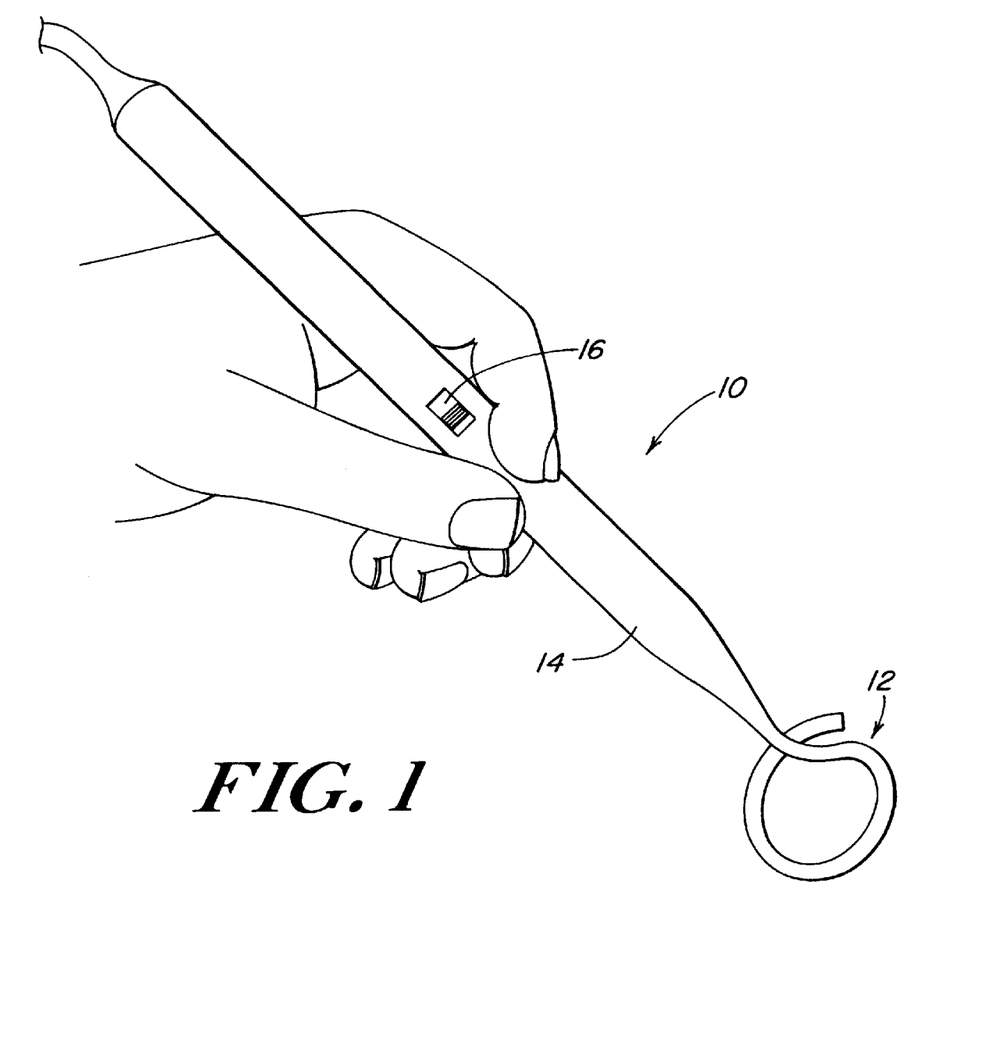
FIG. 1 is a schematic, perspective view of a hand held cardiac ablation instrument in accordance with this invention.

In FIG. 1, a hand held cardiac ablation instrument 10 having a circumferential ablation element 12 is shown. The instrument 10 has a handle 14 for manual placement of element 12 in contact with a targeted tissue area. The handle can have an on/off switch 16. The circumferential ablation element can be in the shape of an open loop so as to allow the loop to be placed around a pulmonary vein or within the heart.

Figure 2:
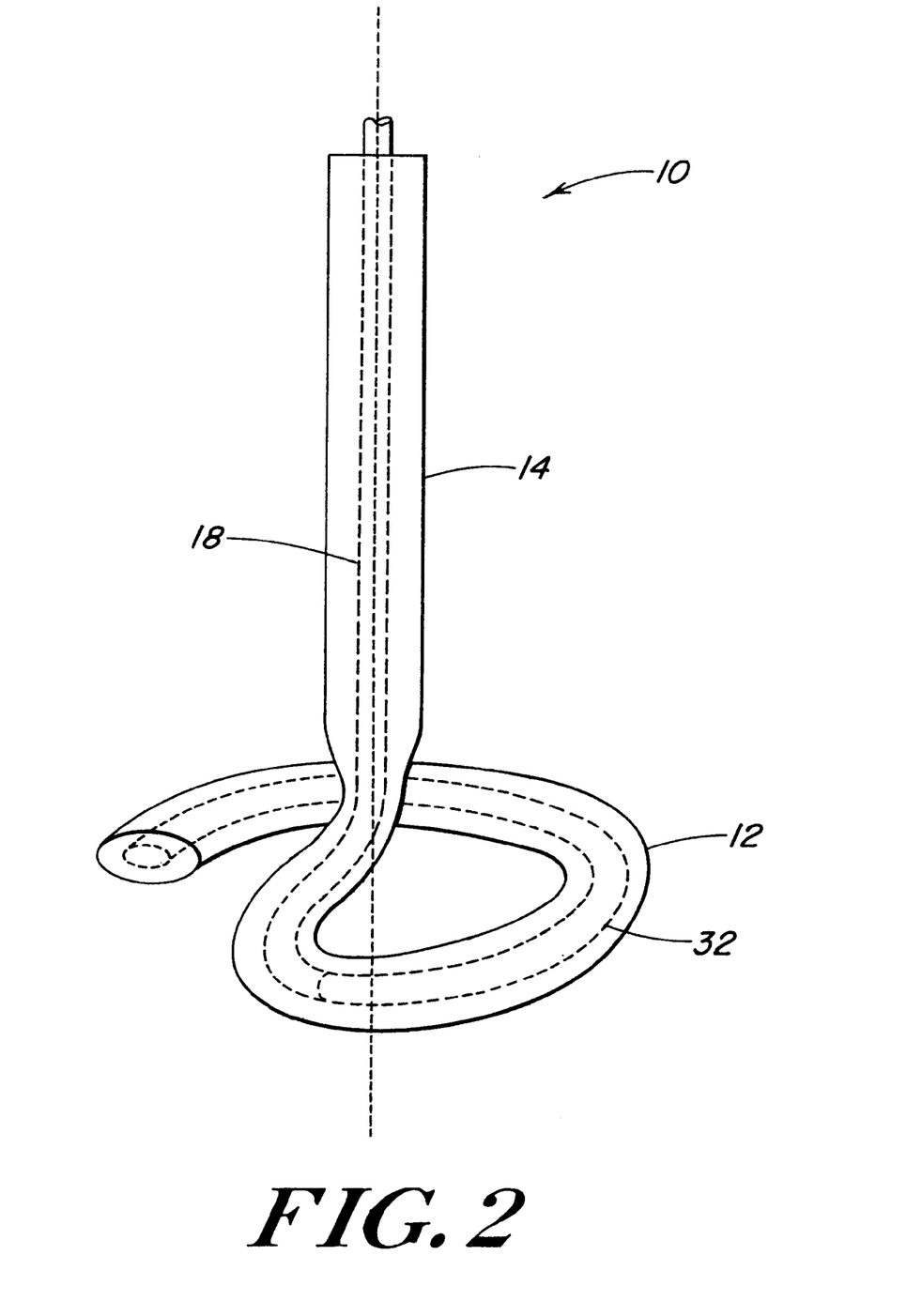
FIG. 2 is another perspective view of the cardiac ablation instrument of FIG. 1.

FIG. 2 shows the cardiac ablation instrument 10 of FIG. 1 having a handle 14 substantially coaxial with the center of the circumferential ablation element 12. Fiber 18 and light diffusing element 32 are shown in phantom.

Figure 3A:
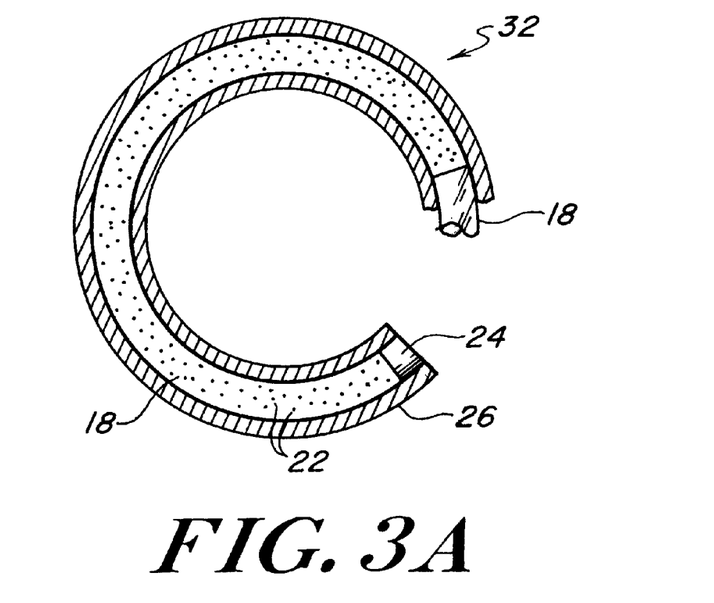
FIG. 3A is a more detailed schematic, cross sectional top view of a circumferentially-shaped ablation element in accordance with the invention.

FIG. 3A is a cross sectional view of the light diffusing element 32, showing a light transmitting optical fiber 18, a scattering medium 28 disposed within a housing 26 and coupled to the optical fiber 18, scattered particles 22, and a reflective end 24. The scattering medium can be a polymeric material having light scattering particles, preferably alumina, silica, or titania compounds, or mixtures thereof The reflective end can be a mirror-coated surface. The light diffusing element can be resiliently deformable to fit around or within a vein or artery.

Figure 3B:
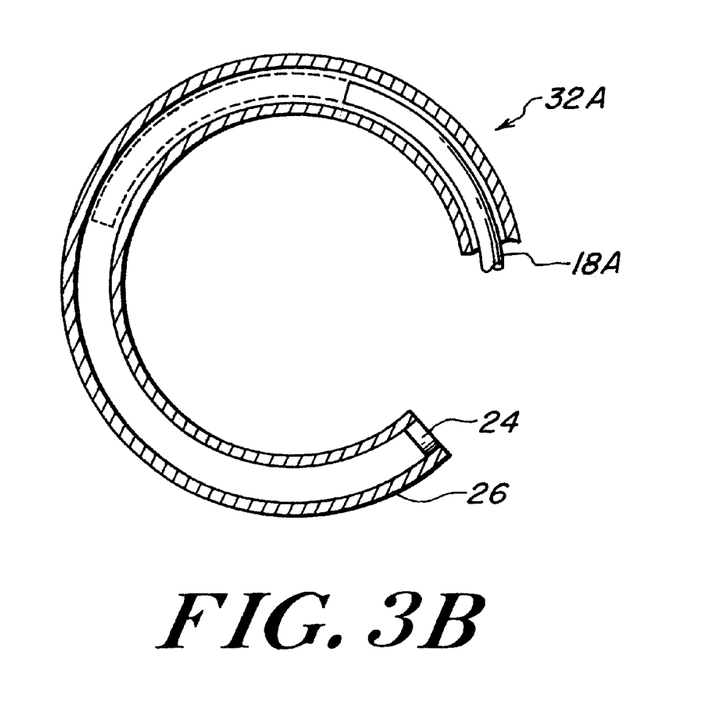
FIG. 3B is another cross sectional top view of an alternative embodiment of the circumferentially-shaped ablation element of FIG. 3A.

FIG. 3B is an alternative embodiment of a light diffusing element 32A, showing a slidable light transmitting optical fiber 18A disposed within the housing 26. The slidably disposed light transmitting optical fiber 18A allows the surgeon to choose the length of the lesion to be created at the targeted site.

Figure 4:
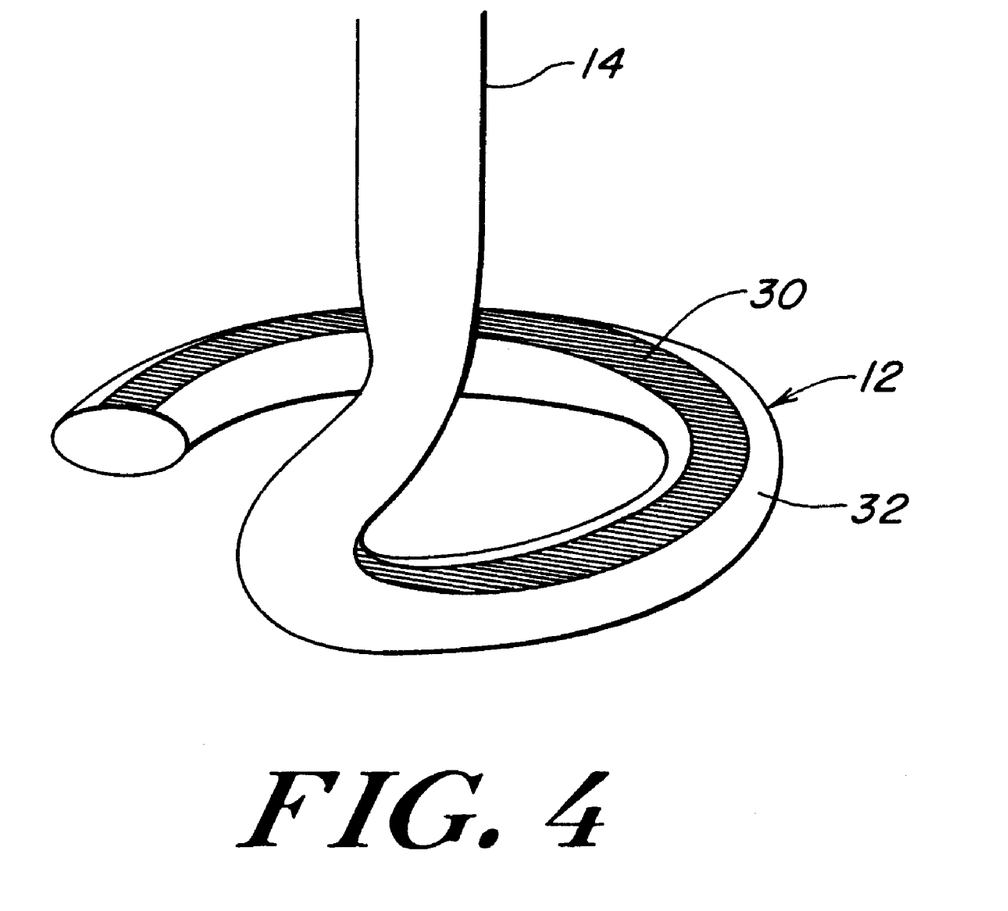
FIG. 4 is a perspective view of an alternative embodiment of the cardiac ablation instrument of FIG. 1.

FIG. 4 shows the cardiac ablation instrument 10 having a light diffusing element 32 coated on one side such that the coating 30 lies substantially diametrically opposed to the target ablation site. The light diffusing element can be coated at different locations relative to the target ablation site.

Light travelling through the optical fibers 18 is transmitted into the housing 26 and scattered in a circular pattern along the length of the ablation element. The housing 26 and the reflective end 24 interact to provide a substantially uniform distribution of light throughout the housing. When a mirrored end cap is employed, light propagating through the ablation element will be at least partially scattered before it reaches the mirror 24. When the light reaches the mirror, it will be reflected by the mirror and returned through the housing. During the second pass, the remaining radiation encounters the scattering medium which provides further circumferential diffusion of the light. When a reflective coating 30 is used, the light propagating through the ablation element is reflected toward the target ablation site to ensure that a uniform lesion is created. For additional details on construction of the light diffusing elements, see U.S. Pat. No. 5,908,415 filed Jun. 1, 1999.

The housing can be made of Teflon® tubes and/or coatings. The use of Teflon® improves the procedures by avoiding the problem of fusion or contact-adhesion between the circumferential ablation element 12 and the cardiac tissue during usage. A resiliently deformable housing can be made of a polymeric, electrically nonconductive material, like polyethylene or polyurethane, which can withstand tissue coagulation temperatures without melting.

Preferred energy sources include laser light, in the range between about 200 nanometers and 2.5 micrometers. In particular, wavelengths that correspond to, or are near, water absorption peaks are often preferred. Such wavelengths include those between about 805 nm and about 1060 nm, preferably between about 900 nm and 1000 nm, most preferably, between about 940 nm and 980 nm. Suitable lasers include excimer lasers, gas lasers, solid state lasers and laser diodes. A particularly preferred AlGaAs diode array, manufactured by Optopower, Tucson, Ariz., produces a wavelength of 980 nm. A preferred energy is coherent light, e.g., laser light, in the range between about 200 nm to about 2.4 micrometers, preferably between about 400 to about 3,000 nm, more preferably between about 805 and 1060 nm. Typically the light diffusing element emits between about 2 to about 10 watts/cm of length, preferably between about 3 to about 6 watts/cm, most preferably about 4 watts/cm.

Figure 5:
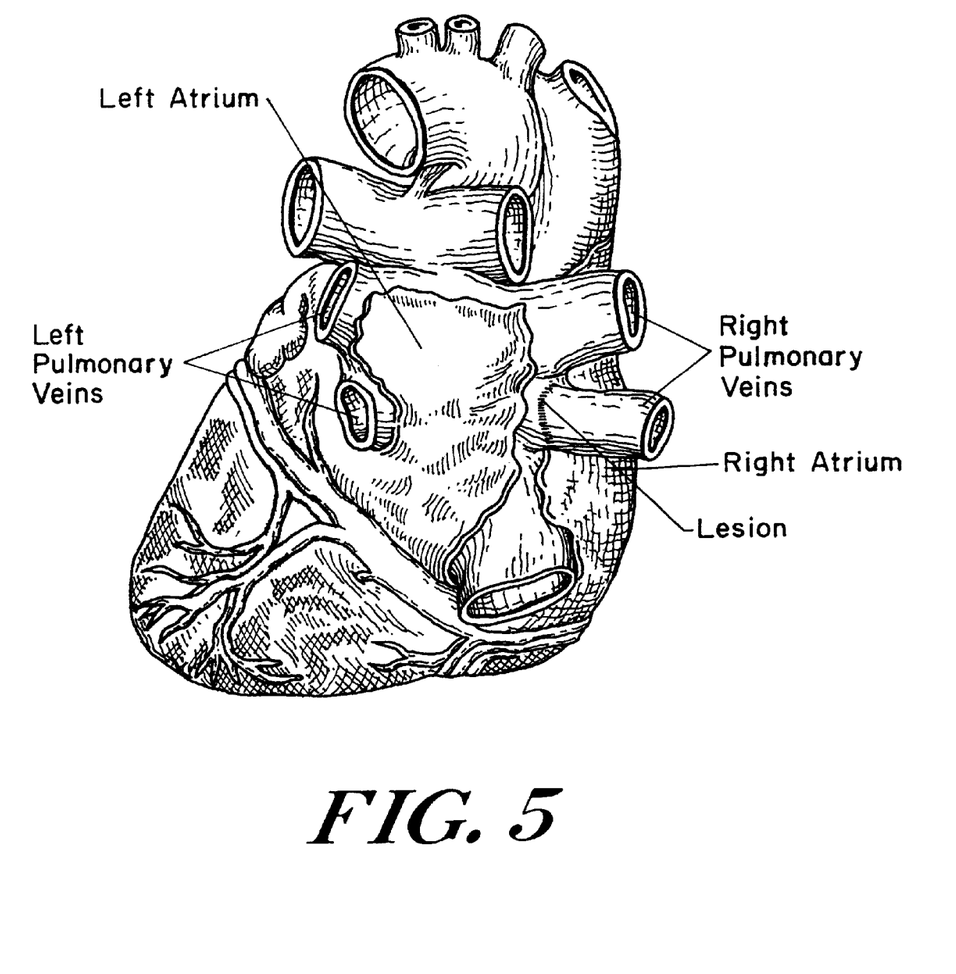
FIG. 5 is a schematic, perspective view of a human heart having ablation lesions.
Figure 6:
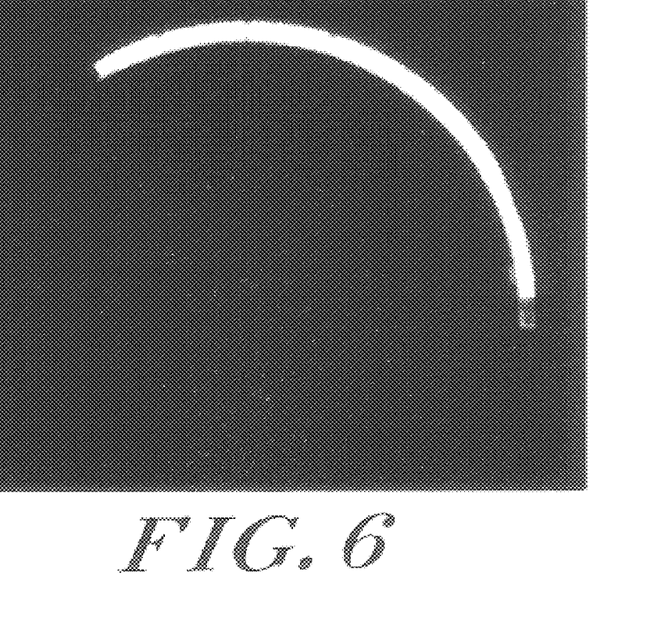
FIG. 6 is a perspective view of an illuminated cardiac ablation instrument in accordance with the present invention.
Figure 7:
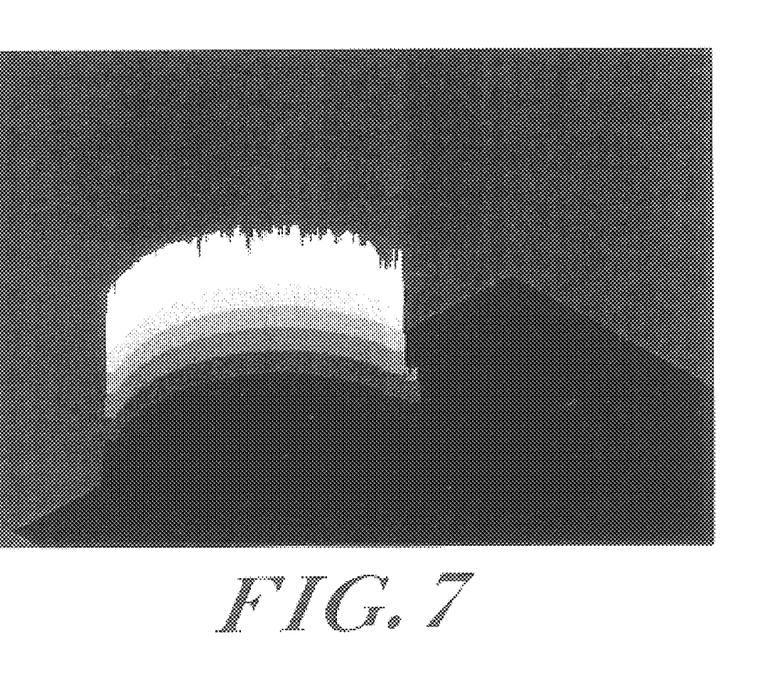
FIG. 7 is a chart showing the intensity curve throughout the light diffusing element of the cardiac ablation instrument of FIG. 1.

In use, the hand held ablation device is coupled to a source of phototherapeutic radiation and positioned within a patient's body either endocardially or epicardially to ablate the tissue. The radiation source is activated to transmit light via the fiber 18 to the circumferential ablation element 12. Radiation is delivered to create a uniform circumferential lesion around a pulmonary vein, as shown in FIG. 5. In mitral valve surgery, radiation is delivered to create several curvilinear lesions, which connect to surround the valves.

What is claimed is:

1. A hand held cardiac ablation instrument comprising:
   a light transmitting optical fiber having a proximal end and a distal end, the proximal end being adapted to receive ablative radiation from a radiation source; and
   a light diffusing element having light scattering medium and being coupled to the distal end of the optical fiber and configured in a toroidal shape to emit an annular pattern of uniform radiation.

2. The instrument of claim 1, wherein the instrument further comprises an optical transparent tubular housing surrounding at least part of the light diffusing element.

3. The instrument of claim 2, wherein the light scattering medium is disposed within a chamber in the housing.

4. The instrument of claim 3, wherein the scattering medium further comprises a polymeric material having light scattering particles incorporated therein.

5. The instrument of claim 3, wherein the scattering medium has a greater refractive index than the housing.

6. The instrument of claim 1, further comprising a handle substantially coaxial the light diffusing element.

7. The instrument of claim 1, wherein the light diffusing element is in the shape of an open loop so as to allow the loop to be placed around or within a pulmonary vein or artery.

8. The instrument of claim 7, wherein the diameter of the loop is between 10 and 50mm.

9. The instrument of claim 7, wherein the width of the diffusing element is between 1 and 5 mm.

10. The instrument of claim 2, wherein the housing comprises a fluorocarbon polmer.

11. The instrument of claim 4, wherein the light scattering particles are chosen from the group consisting of alumina, silica, and titania compounds and mixtures thereof.

12. The instrument of claim 2, wherein the tubular housing further comprises a distal reflective surface.

13. The instrument of claim 12, wherein the reflective surface comprises a mirror coated surface.

14. The instrument of claim 12, wherein radiation propagating through the fiber enters the scattering medium and a portion of the radiation is scattered outward through the housing, and another portion passes through the scattering medium and is reflected by the reflective surface for retransmission through the scattering medium.

15. The instrument of claim 14, wherein the scattering medium and the reflective end surface interact to provide a substantially uniform axial distribution of radiation over the length of the housing.

16. The instrument of claim 2, wherein the tubular housing is partially coated with a reflective surface substantially diametrically opposed to a target ablation site.

17. The instrument of claim 16, wherein the reflective surface comprises a mirror coated surface.

18. The instrument of claim 16, wherein the reflective surface is gold.

19. The instrument of claim 16, wherein the scattering medium and the reflective surface interact to provide a substantially uniform axial distribution of radiation over the length of the housing to a target ablation site.

20. A hand held cardiac ablation instrument comprising:
    a slidably disposed light transmitting optical fiber;
    a housing in the shape of an open toroidal loop having a first end adapted to receive the slidably disposed light transmitting optical fiber; and
    at least one diffuser chamber coupled to the fiber within the housing.

21. The instrument of claim 20, wherein the diffuser chamber comprises light scattering medium disposed within the housing and coupled to the slidably disposed light transmitting optical fiber.

22. The instrument of claim 20, wherein the scattering medium further comprises a polymeric material having light scattering particles incorporated therein.

23. The instrument of claim 20, wherein the light scattering particles are chosen from the group consisting of alumina, silica, and titania compounds and mixtures thereof.

24. The instrument of claim 20, wherein the housing further comprises a second end with a reflective surface.

25. The instrument of claim 24, wherein the reflective surface comprises a mirror coated surface.

26. The instrument of claim 20, wherein the tubular housing is partially coated with a reflective surface substantially diametrically opposed to a target ablation site.

27. The instrument of claim 26, wherein the reflective surface comprises a mirror coated surface.

28. The instrument of claim 26, wherein the reflective surface is gold.

29. The instrument of claim 20, wherein the scattering medium and the reflective surface interact to provide a substantially uniform axial distribution of radiation over the length of the housing to a target ablation site.

30. A method of ablating cardiac tissue, comprising:
    positioning a device in proximity to a target region of cardiac tissue, the device having a light diffusing element coupled to a source of photoablative radiation and configured in a toroidal shape to emit an arcuate pattern of radiation;
    applying the device to the target region to induce an curvilinear lesion;
    moving the device to a second position;
    reapplying the device to the target region to induce a second curvilinear lesion;
        repeating the steps of positioning and applying until the lesions are joined together to create a composite circumferential lesion.

31. The method of claim 30, wherein the device is positioned endocardially.

32. The method of claim 30, wherein the device is positioned epicardially.

* * * * *